United States Patent [19]

Mercer et al.

[11] 4,371,338

[45] Feb. 1, 1983

[54] DENTAL ARTICULATOR HAVING SIMPLIFIED MEANS FOR MOUNTING DENTAL CASTS

[76] Inventors: Roger W. Mercer, 1340 Arlington Dr., Fairborn, Ohio 45324; Louis E. Hay, 847 Woodhill Rd., Dayton, Ohio 45431

[21] Appl. No.: 56,536

[22] Filed: Jul. 11, 1979

[51] Int. Cl.³ .............................................. A61C 11/00
[52] U.S. Cl. ...................................................... 433/60
[58] Field of Search ...................................... 433/60, 64

[56] References Cited

U.S. PATENT DOCUMENTS 2,621,407  12/1952  Schlesinger .......................... 433/60
3,844,040  10/1974  Willis ..................................... 433/60

*Primary Examiner*—Robert Peshock
*Attorney, Agent, or Firm*—Louis E. Hay

[57] ABSTRACT

A dental articulator for mounting and adjusting paired dental casts; said articulator having at least one protruding locating pin entering an aperture in the base of each dental cast and having fastening means other than conventional mounting plaster for releasably retaining the dental casts in their mounted position; and further having means for adjusting the upper dental cast in centric anatomical relationship with the lower dental cast.

2 Claims, 6 Drawing Figures

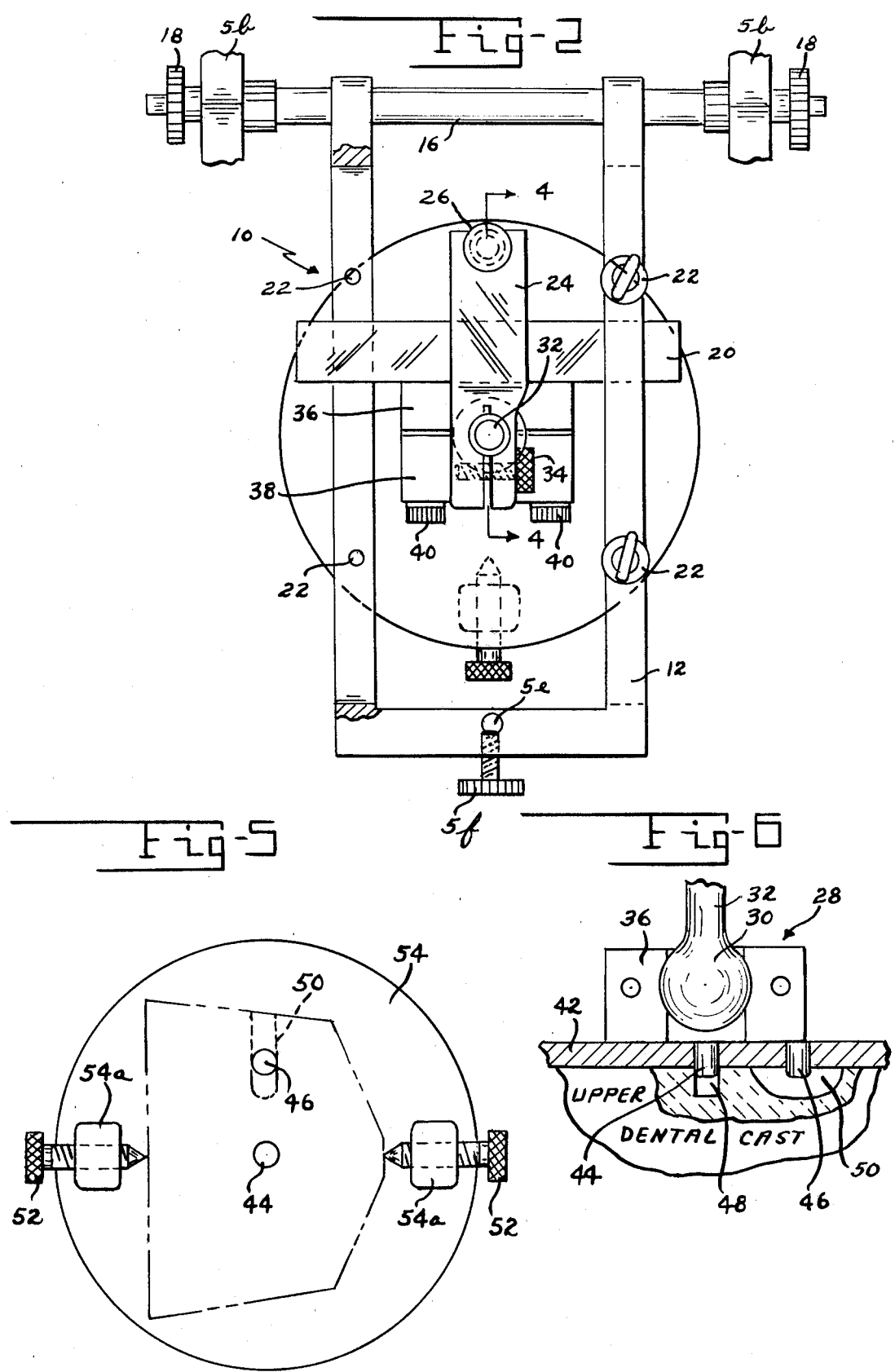

DENTAL ARTICULATOR HAVING SIMPLIFIED MEANS FOR MOUNTING DENTAL CASTS

REFERENCE TO RELATED U.S. PATENTS

U.S. Pat. No. 3,975,489 Cast Ejector, relating to a method of embedding a threaded plastic button into the base of a dental cast.

U.S. Pat. No. 4,169,314 Dental Articulator For Mounting Casts Without Plaster, relating to an adjustable articulator mounting dental casts with screws engaging a threaded aperture in the base of each dental cast.

REFERENCE TO RELATED U.S. PATENT APPLICATION

Ser. No. 788,236 Apparatus And Method For Mounting Dental Casts, filed Apr. 18, 1977 and relating to a design of dental articulator for mounting dental casts having a threaded aperture in the base thereof.

BACKGROUND OF THE INVENTION

Dental articulators are a common and necessary apparatus in the fabrication of a dental prosthesis. Stripped to its bare essentials, the process of fabricating a prosthesis commences when the dentist takes impressions of the patient's maxillary and mandibular arches which may or may not include some natural teeth. These impressions are negative imprints of the arches and become the molds into which the raw material for forming positive dental casts are poured. These positive casts are duplicates of the patient's arches (with or without teeth) and become the primary model to which the prosthesis is to be constructed.

In order to construct an acceptable prosthesis, these dental casts are normally mounted in a dental articulator in order that the maxillary and mandibular casts are maintained in the same anatomical relationship as in the mouth of the patient. This is true in all cases even those where only one prosthesis, as for example the maxillary arch is to be constructed, since the prosthesis must also conform with the relating surfaces on the mandibular arch in the patient's mouth.

Another reason why the dental casts are mounted in an articulator is to permit arrangement of the denture (false) teeth in their proper position for occlusion. On partial dentures, the occlusion of the denture teeth must be with natural teeth. On full dentures greater liberty is often taken to improve function and esthetics. The desired occlusion not only includes the vertical bite but also a degree of lateral movement as well as posterior and anterior movement of the lower jaw. These various movements are produced by the temporomandibular joint which is the joint formed by the condyle of the mandible and the temporal bone. Many dental articulators are built to simulate these movements to a high degree.

Past practice for countless years has been to mount the dental casts in the articulator by means of plaster which is usually a gypsum material. This locates the dental casts in a fixed position. Mounting the dental casts by means of plaster is relatively expensive, is dusty and time consuming because the powdered raw material must be thoroughly mixed with a liquid and the plaster must be allowed to set, the process is subject to error which cannot be compensated, and all utensils must be thoroughly cleaned after each use. Even in cases where the dental casts have been provided with grooves to facilitate removal and remounting which is often a requirement in the fabrication process, it is questionable at best whether or not the casts were remounted to their precise originally mounted positions.

At least 95% of all dental articulators built to date have been built for use with plaster mounting techniques. A few have been built which use mechanical mounting devices such as claws or other clamping devices in an attempt to find a better mounting technique than by the use of plaster. These alternate mounting techniques have been far less satisfactory than plaster, especially in those situations where the dental casts are to be removed and remounted to their original positions.

The above referenced U.S. Pat. No. 4,169,314 and U.S. patent application are the first known articulators mounting dental casts without the use of mounting plaster and having the required precision for the most exacting requirements in the fabrication of dental prostheses.

With the exception of the above referenced articulators, all prior known articulators which mounted dental casts by mechanical means in lieu of mounting plaster did so by means of clamping devices around the periphery of the dental casts. Their greatest weakness is their inability to permit removal of the dental casts from the articulator and then subsequently remounting the casts to their precise original position. This is an absolute requirement except for the more simple crown and bridge work. Although such articulators permit the mounting of dental casts in a relatively fast manner, their lack of precision is the primary cause for their low acceptance by the dental profession. The clamps all worked like a vise in which the dental casts were clamped. As the plaster of which the dental casts are made is mechanically abraded by the clamps, the position of the dental casts will shift in the articulator.

The above referenced articulators solved the problem by locating on fixed points such as the threaded aperture in the base of the dental casts, or by an embedded button having a threaded aperture. The holding or retaining means of these articulators do not disturb these fixed locating points and dental casts are easily remounted to their precise original position.

The present invention is a further simplification of the mechanical mounting of dental casts having fixed locating apertures in the base of the dental casts. Instead of using threaded apertures as in the above referenced articulators, the articulator of the present invention uses unthreaded apertures which are easier and faster to form. The dental casts may be poured in the same manner they have been poured for years (that is without threaded embedded buttons) and the apertures are easily formed in the dental laboratory on a dental lathe which is in every laboratory. One aperture is preferably a round aperture in the central portion of the dental cast and the second aperture is preferably a radial slot, each of the apertures to receive a locating pin protruding from a flat surface on the articulator. The central pin is the principal pin and prevents all movement of the dental cast except rotational movement. The pin engaging the radial aperture in the dental cast prevents rotational movement of the cast. It takes very little holding force to retain the dental casts in their mounted position. There are numerous methods by which the dental casts may be retained. One very simple and effective method is depicted in the drawings.

BRIEF DESCRIPTION OF THE DRAWINGS

FIG. 2 is a plan view of the upper mounting jig;

FIG. 5 is a plan view taken along line 5—5 of FIG. 1 and showing locating pins engaging apertures in the base of a dental cast; and, FIG. 6 is a vertical section taken along line 6—6 of FIG. 1 and showing details of a typical wobble plate with protruding locating pins engaging apertures in the base of a dental cast.

DESCRIPTION OF THE PREFERRED EMBODIMENT

At the onset it should be noted that the lower mounting jig may or may not be provided with rotational movement, and with or without vertical movement; and that the upper mounting jig is provided with anterior-posterior movement, with lateral movement, with vertical movement, with rotational movement, and with canting movement by means of a wobble plate assembly.

Figure 1:
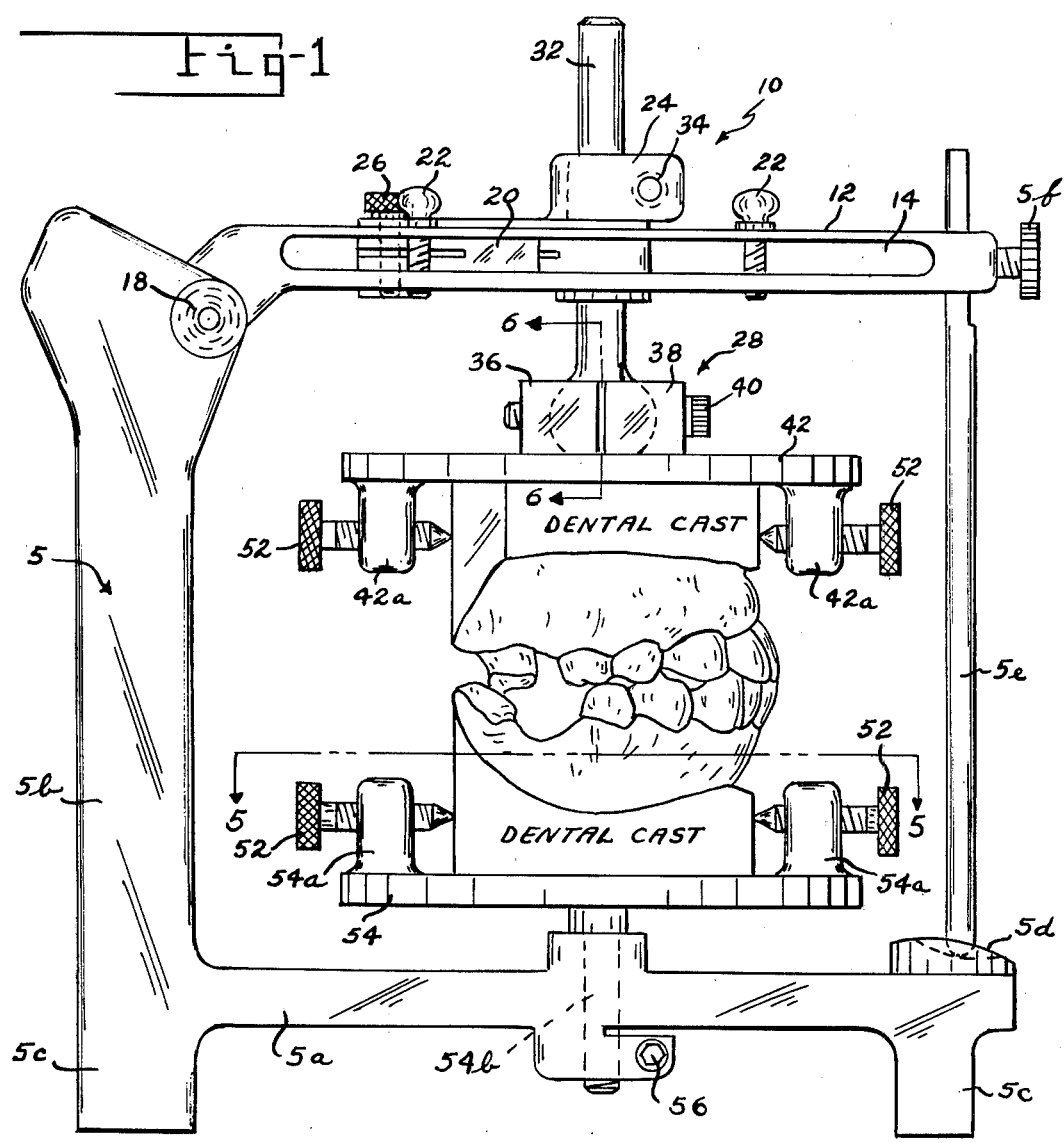
FIG. 1 is a side elevation of a dental articulator supporting an upper and a lower mounting jig to which a matched set of dental casts are mounted and held in their occlusion position.

Specific reference is made to FIGS. 1 and 2 which depict an upper and a lower dental cast mounting jig joined to a suitable articulator body to form a composite dental articulator for the mounting and adjusting of a matched set of dental casts in their correct anatomical occlusion position in relationship with each other.

The articulator body 5 has a horizontal base 5a, two vertical upright members 5b, a plurality of suitable feet 5c providing clearance for portions of the lower mounting jig which extend below the base, and an incisal table 5d.

The pivoted upper leaf of the conventional dental articulator, which usually is provided with luting slots, is replaced with an upper dental cast mounting jig 10 in accordance with the present invention. As indicated, the rear portion of the mounting jig is pivotally joined to the upper portion of the vertical upright member 5b of the articulator body and has a normally horizontal position superimposed over base 5a.

The usual adjustable incisal pin 5e is adjustably retained by the upper mounting jig 10 where it is retained by screw 5f. The functions and use of the incisal pin and incisal table are well known in the dental art and need not be further explained.

The upper dental cast mounting jig 10 is provided with a redesigned leaf which is preferably in the form of a U-shaped frame member 12 having two side elements containing elongated slots 14. The open end of the frame member 12 is joined to a shaft 16, which in turn is pivotally supported by the vertical upright member 5b of the articulator body, and held in place by retaining nuts 18.

A transverse bar member 20 is slidably supported within the elongated slots 14 of the frame member 12. The transverse bar member 20 is free to slide fore and aft within the slots and thereby establishes the anterior-posterior position of the upper dental cast in relationship with the lower dental cast. The bar member 20 is retained in its proper adjusted position by tightening screws 22. If desired, suitable stops (not shown) which are well known to the mechanical arts may be provided to prevent the transverse bar member from laterally sliding out of the frame member. If desired, and within the scope of the present invention, other arrangements may be used for supporting and adjusting the position of the transverse bar in relationship with the frame member.

Figures 3, 4:
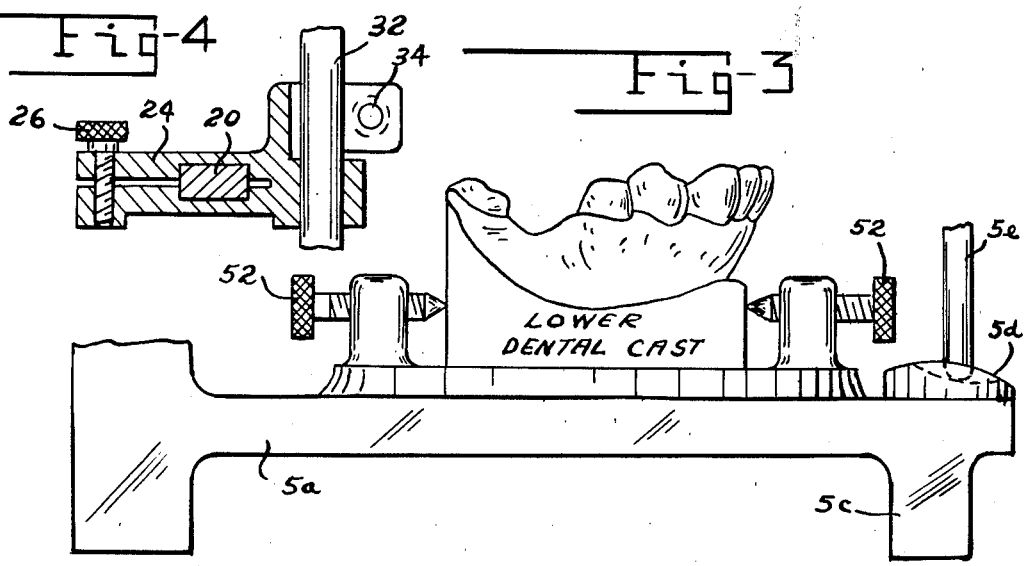
FIG. 3 is an alternate design of the base portion of the articulator depicted in FIG. 1 and showing the lower dental cast mounted directly to the base element of the articulator body.
FIG. 4 is a vertical section taken along line 4—4 of FIG. 2 and showing details of the lateral movement block.

A lateral movement block member 24 is slidably supported by the transverse bar member 20 as shown in FIGS. 1, 2 and 4. The lateral movement block member is free to slide to the proper lateral occlusion position of the dental casts, in which position it may be retained by tightening screw 26.

A wobble plate assembly 28, as best shown in FIGS. 1 and 6, is slidably and rotatably retained by the lateral movement block 24. Referring specifically to FIG. 6, a ball 30, having an upward extending stem 32, is slidably retained in a bore of lateral movement block 24 as best shown in FIG. 4. Within the scope of the present invention, the stem 32 may be threaded for engaging a threaded bore in the lateral movement block. A split clamp may be made integral with the lateral movement block 24 as also shown in FIG. 4. The vertical position of stem 32 in relationship with the lateral movement block 24 controls the vertical adjustment of the upper dental cast in relationship with the lower dental cast. The adjusted position may be retained by tightening screw 34.

Again referring specifically to FIG. 6, the ball 30 is surrounded by a vertically split socket comprising a fixed socket half 36 and a movable socket half 38. The two socket halves are retained in their relative position and are tightened against the ball 30 by means of screws 40 which pass through movable socket half 38 and engage threads in the fixed socket half 36.

The fixed socket half is joined to the upper face of wobble plate 42. The fixed socket half may be joined to the wobble plate by brazing or welding as indicated, or, it may be joined by screws, rivets, or other means well known to the mechanical arts. The movable socket half slides on top of the wobble plate and is free to slide when one or both of the screws 40 are slightly loosened. Rotational movement of the upper dental cast may be attained by movement about ball 30, or, by rotational movement of stem 32 in the lateral movement block 24; or, by movement at both places.

As depicted in FIGS. 5 and 6, a locating pin 44 protrudes from the central area of wobble plate 42 in the direction of the dental cast to be mounted. A second locating pin 46 is located at a convenient distance from the central locating pin 44 and protrudes in the same direction as the first pin.

Both pins engage apertures formed in the base of the dental cast to be mounted. The central locating pin 44 engages a round aperture 48 in the dental cast. The second locating pin preferably engages an elongated radial slot 50 as depicted in FIGS. 5 and 6. The radial slot may be as depicted in FIG. 6, or as an alternative, the radial slot may be extended to the edge of the cast as depicted in FIG. 5.

The apertures may be formed into the base of a dental cast by several methods. One method is to form the apertures in the dental cast at the time the casts are poured. Suitable male cores to form the apertures may be attached to a slab such as slab 34 depicted in FIG. 12 of the referenced U.S. Pat. No. 3,975,489. Another method is to machine the apertures into the base of dental casts formed in the conventional manner. After the base of the casts has been surfaced on a disc sander the apertures may be machined on a dental lathe. The central round aperture 48 may be cut with an ordinary burr or drill, and the radial slot 50 may be cut with an abrasive disc of proper width; such cutting tools already being in use in all dental laboratories. Apertures machined in this manner are found to be true to size and without abrading at the edges.

The central pin 44 is the principal locating pin which prevents all movement of the dental cast on the wobble plate with the exception of rotational movement. The second locating pin 46 prevents rotational movement of the cast. The apertures in the base of the casts may be at any convenient location, those depicted being for illustrative purposes only.

The wobble plate 42 is provided with two protruding lugs 42a which may be integral with the wobble plate, or, which may be discrete elements joined to the wobble plate. After the dental cast is properly located on the locating pins, the cast is held in place by screws 52.

It requires a surprisingly small amount of pressure to hold the dental casts in place. Screws with several types of ends were tried and it was found that conically pointed screws and screws having swivel feet work very well. The important thing is that the dental casts remains against the wobble plate without separation when the screws are tightened. If desired, the screws, which are depicted to be horizontal, may be tilted at about 10 degrees to produce a vertical thrust component. Within the scope of the invention, any means for holding the dental casts may be used, including rubber bands, garter springs, and spring biased clamping arrangements. Also within the scope of the invention, the upper cast mounting jig may be built to fit the leaf on some existing articulators. The upper mounting jig depicted in the referenced application Ser. No. 788,236 was built to fit a standard KSK articulator.

The lower dental cast may be mounted on a movable platform as depicted in FIG. 1, or, it may be mounted in fixed position on the base of the articulator as depicted in FIG. 3.

The movable platform or lower mounting jig 54 depicted in FIG. 1 is substantially the same size as wobble plate 42. The platform has protruding lugs 54a which are comparable to protruding lugs 42a on the wobble plate. The platform also has protruding locating pins (not shown) which are comparable to locating pins 44 and 46 in the wobble plate for engaging apertures in the lower dental cast which is held in position by screws 52.

The horizontal platform or lower mounting jig 54 has a circular elongated stem as indicated by 54b in FIG. 1; the stem passing through a bore in base 5a of the articulator body. The lower mounting jig 54 may be rotated to any desired position and retained by tightening screw 54 which engages a split clamp such as is also used on the lateral movement block 24 as shown in FIG. 4. In addition to rotational movement, the lower mounting jig is capable of vertical movement if desired. Within the scope of the present invention, the stem 54b may be threaded for engaging a threaded bore in the base of the articulator body.

An alternate design of the lower mounting jig is depicted in FIG. 3. This design is less expensive to build than the design depicted in FIG. 1 and may be used by technicians who do not insist on rotational and vertical adjustability for the lower dental cast. This jig includes the same locating pins (not shown) as those depicted in FIGS. 5 and 6, and the dental cast is located and held in position in the same manner as was previously described.

The upper and lower mounting jigs should each have two locating pins as depicted and described in those articulators in which dental casts are to be mounted, removed for thermal curing of the dentures and then remounted to the precise original position for articulation of the dentures which were fabricated on the dental casts. It has been found to be advantageous to cut slots 50 to the edge of the dental casts as depicted in FIG. 5 since this will facilitate the ease with which the casts may be positioned on the locating pins.

On articulators in which the dental casts are not removed until the final denture has been fabricated, as for example in crown and bridge work which does not include an acrylic portion requiring thermal curing, only a central locating pin 44 is required.

Within the scope of the present invention, the wobble plate 42 of the upper mounting jig and the platform 54 of the lower mounting jig as depicted in FIGS. 1 and 5 may each comprise a single plate with pin/pins protruding as illustrated, or, one or both may have a second plate detachably joined to the first plate in face to face relationship and carrying the protruding pin/pins. In like manner, the fastening means for detachably retaining the dental casts may be carried by the single plate as illustrated, or, the fastening means may be carried by the second plate.

Also within the scope of the present invention, an elongated vertical slot may be cut through the central portion of transverse bar 20 and the vertical bore in the lateral movement block 24 may be located to be in alignment with such elongated slot, thus permitting stem 32 to pass through the transverse bar in lieu of being adjacent as depicted in the drawings.

Although in the human body the upper teeth are stationary and the jaw moves the lower teeth in relationship to the upper teeth, for practical reasons in articulators the movement is usually reversed and the upper dental cast is adjusted to centric anatomical relationship with the lower dental cast. It is obvious that within the scope of the present invention, the lower mounting jig may be provided with all the movements of the depicted upper mounting jig, and that the position of the depicted mounting jigs may be reversed.

It is to be understood that the embodiments of the present invention as shown and described is to be regarded merely as illustrative, and that the invention is susceptible to variations, modifications and changes without regard to construction methods, within the scope of the appended claims.

We claim:
1. A dental articulator for mounting and adjusting matched upper and lower dental casts having at least one unthreaded aperture in the base of said dental casts, said articulator comprising:
  (a) an articulator body having a base element and at least one vertical element extending upward from said base element;
  (b) a lower dental cast mounting jig supported by the base element of said articulator body, said mounting jig having at least one upward protruding locating pin for engaging an aperture in the base of said lower dental cast and locating said lower dental cast in mounted position on said mounting jig, and further having fastening means for releasably retaining said lower dental cast in mounted position on said mounting jig; and, (c) an upper dental cast mounting jig for mounting and adjusting said upper dental cast in centric anatomical relationship with said lower dental cast, said upper mounting jig having a normally horizontal frame member with spaced apart elongated side elements and being pivotally joined to the vertical element of said articulator body to be superimposed with the base element of said articulator body, an elongated transverse bar member spanning the side elements of said frame member and being retainably movable fore and aft with the side elements of said frame member for providing anterior-posterior movement of said upper dental cast in relationship with said lower dental cast, a lateral movement block member longitudinally and retainably slidable on said transverse bar member for providing lateral movement of said upper dental cast in relationship with said lower dental cast and having a vertical bore therethrough, a vertical movement member retainably movable in the vertical bore of said lateral movement block member for providing vertical movement of said upper dental cast in relationship with said lower dental cast, a dependent wobble plate assembly operably attached to said vertical movement member for providing retainable rotational and canting movement of said upper dental cast in relationship with said lower dental cast, said wobble plate assembly having at least one downward protruding locating pin for engaging an aperture in the base of said upper dental cast and locating said upper dental cast in mounted position on said wobble plate assembly, and fastening means for releasably retaining said upper dental cast in mounted position on said wobble plate assembly.

2. A dental articulator for mounting and adjusting matched upper and lower dental casts having at least one unthreaded aperture in the base of said dental casts, said articulator comprising:

(a) an articulator body having a base element and at least one vertical element extending upward from said base element;

(b) a lower dental cast mounting jig supported by the base element of said articulator body, said mounting jig having at least one upward protruding locating pin for engaging an aperture in the base of said lower dental cast and locating said lower dental cast in mounted position on said mounting jig, fastening means for releasably retaining said lower dental cast in mounted position on said mounting jig, and further having means for adjusting said mounting jig in relationship with the base element of said articulator body; and, (c) an upper dental cast mounting jig for mounting and adjusting said upper dental cast in centric anatomical relationship with said lower dental cast, said upper mounting jig having a normally horizontal frame member with spaced apart elongated side elements and being pivotally joined to the vertical element of said articulator body to be superimposed with the base element of said articulator body, an elongated transverse bar member spanning the side elements of said frame member and being retainably movable fore and aft with the side elements of said frame member for providing anterior-posterior movement of said upper dental cast in relationship with said lower dental cast, a lateral movement block member longitudinally and retainably slidable on said transverse bar member for providing lateral movement of said upper dental cast in relationship with said lower dental cast and having a vertical bore therethrough, a vertical movement member retainably movable in the vertical bore of said lateral movement block member for providing vertical movement of said upper dental cast in relationship with said lower dental cast, a dependent wobble plate assembly operably attached to said vertical movement member for providing retainable rotational and canting movement of said upper dental cast in relationship with said lower dental cast, said wobble plate assembly having at least one downward protruding locating pin for engaging an aperture in the base of said upper dental cast and locating said upper dental cast in mounted position on said wobble plate assembly, and fastening means for releasably retaining said upper dental cast in mounted position on said wobble plate assembly.

* * * * *